US012779117B2

(12) United States Patent
Yang

(10) Patent No.: US 12,779,117 B2
(45) Date of Patent: *Nov. 3, 2026

(54) BILATERALLY DRIVEN DRUG INFUSION SYSTEM

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 562 days.

This patent is subject to a terminal disclaimer.

(21) Appl. No.: 18/036,650

(22) PCT Filed: Aug. 23, 2021

(86) PCT No.: PCT/CN2021/114042

§ 371 (c)(1),
(2) Date: May 12, 2023

(87) PCT Pub. No.: WO2022/116602

PCT Pub. Date: Jun. 9, 2022

(65) Prior Publication Data

US 2024/0009386 A1 Jan. 11, 2024

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14503* (2013.01); *A61B 5/14532* (2013.01);
(Continued)

(58) Field of Classification Search
CPC ...... A61M 5/1723; A61M 5/14; A61M 5/142; A61M 5/14248; A61M 5/1452;
(Continued)

(56) References Cited

U.S. PATENT DOCUMENTS 12,102,792 B2 * 10/2024 Yang ................. A61M 5/14236
2005/0238507 A1 * 10/2005 Dilanni ..................... F04B 9/08
417/415
(Continued)

FOREIGN PATENT DOCUMENTS

CN 108261585 7/2018
CN 108281200 7/2018
(Continued)

OTHER PUBLICATIONS

"International Search Report (Form PCT/ISA/210) of PCT/CN2021/114042," mailed on Nov. 23, 2021, pp. 1-3.

*Primary Examiner* — Theodore J Stigell
(74) *Attorney, Agent, or Firm* — JCIP GLOBAL INC.

(57) ABSTRACT

A bilaterally driven drug infusion system, includes: an infusion unit, including a drug storage unit; a piston and a driving wheel respectively connected with a screw, the driving wheel, provided with wheel teeth, driving the screw movement by rotation, the piston arranged in the drug storage unit, the screw advancing the piston to move; a driving unit, cooperated with the driving wheel; a power unit, connected to the driving unit; a control unit, controlling the driving unit to output forces in two different directions on the driving unit; and sensing unit, operatively connected to the control unit and used to sense or recognize the user's body movements, and different body movements represent different functional instructions, and according to the body movement sensed or recognized by the sensing unit, the control unit controlling the infusion unit to execute corresponding functional instructions.

12 Claims, 10 Drawing Sheets

(51) Int. Cl.

*A61B 5/145* (2006.01)
*A61M 5/14* (2006.01)
*A61M 5/142* (2006.01)
*A61M 5/145* (2006.01)
*A61M 5/168* (2006.01)
*G16H 20/17* (2018.01)

(52) U.S. Cl.

CPC ............ *A61B 5/746* (2013.01); *A61B 5/7475* (2013.01); *A61M 5/14* (2013.01); *A61M 5/142* (2013.01); *A61M 5/14248* (2013.01); *A61M 5/1452* (2013.01); *A61M 5/16804* (2013.01); *A61M 5/16831* (2013.01); *G16H 20/17* (2018.01); *A61B 2562/0219* (2013.01); *A61M 2005/14208* (2013.01); *A61M 2205/103* (2013.01); *A61M 2205/276* (2013.01); *A61M 2205/33* (2013.01); *A61M 2209/01* (2013.01); *A61M 2230/201* (2013.01)

(58) Field of Classification Search

CPC .......... A61M 5/16804; A61M 5/16831; A61M 2005/14208; A61M 2205/103; A61M 2205/276; A61M 2205/33; A61M 2209/01; A61M 2230/201; A61M 2005/1726; A61M 2230/005; A61M 2230/62; A61M 2205/3584; A61M 2230/63; A61M 2205/18; A61M 2205/3334; A61B 5/14503; A61B 5/14532; A61B 5/746; A61B 5/7475; A61B 2562/0219; A61B 2560/0443; A61B 2560/045; A61B 5/0004; A61B 5/1118; A61B 5/1126; A61B 5/721; G16H 20/17; H04L 2209/88; H04L 9/3231

See application file for complete search history.

(56) References Cited

U.S. PATENT DOCUMENTS

| | | | | |
|---|---|---|---|---|
| 2007/0124002 | A1* | 5/2007 | Estes | A61M 5/172 700/20 |
| 2016/0158437 | A1* | 6/2016 | Biasi | F04B 43/0072 417/279 |
| 2016/0228633 | A1* | 8/2016 | Welsch | G06F 3/015 |
| 2017/0173262 | A1* | 6/2017 | Veltz | G16H 20/17 |
| 2019/0099551 | A1* | 4/2019 | Yodfat | A61M 5/16831 |
| 2020/0101223 | A1 | 4/2020 | Intereur et al. | |
| 2021/0100951 | A1* | 4/2021 | Chase | A61M 5/1723 |

FOREIGN PATENT DOCUMENTS

| | | |
|---|---|---|
| WO | 2019246217 | 12/2019 |
| WO | 2020232565 | 11/2020 |
| WO | 2020233484 | 11/2020 |
| WO | 2020233486 | 11/2020 |

* cited by examiner

BILATERALLY DRIVEN DRUG INFUSION SYSTEM

CROSS-REFERENCE TO RELATED APPLICATION

This application is a 371 of international application of PCT application serial no. PCT/CN2021/114042, filed on Aug. 23, 2021, which claims the priority benefit of China application no. PCT/CN2020/133734, filed on Dec. 4, 2020. The entirety of each of the above-mentioned patent applications is hereby incorporated by reference herein and made a part of this specification.

TECHNICAL FIELD

The present invention mainly relates to the field of medical instruments, in particular to a bilaterally driven drug infusion system.

BACKGROUND

A bilaterally driven drug infusion system is a medical device that achieves treatment of a patient's physiological condition by continuously injecting a drug into a patient. Bilaterally driven drug infusion system is widely used for the treatment of diabetes, allowing required doses of insulin to be continuously infused into the subcutaneous tissue of the patient's body, thereby simulating the secretion function of the pancreas, thereby keeping the patient's blood sugar stable. The drug fluid is usually stored inside the infusion pump. The existing bilaterally driven drug infusion system usually attaches the pump body directly to the patient's body through a medical adhesive tape, and the patient operates a remote device to control infusion.

Currently, when a user uses an infusion system, he needs to find different inputting positions on the remote device to manually input functional instruction, and then control the infusion pump to perform corresponding functions. This inputting process is cumbersome, which worsens the user experience infusion system.

Therefore, in the prior art, there is an urgent need for an infusion system that simplifies the functional instruction inputting process and has a better user experience.

BRIEF SUMMARY OF THE INVENTION

The embodiment of the invention discloses a bilaterally driven drug infusion system, the user's body movement, as a functional instruction, is sensed by a sensing unit, the control unit can control the infusion unit to execute the corresponding function without the user manually inputting the functional instruction on the remote device, enhancing the user experience.

The invention discloses a bilaterally driven drug infusion system, comprising: comprising: an infusion unit, includes a drug storage unit; a piston and a driving wheel respectively connected with a screw, the driving wheel, provided with wheel teeth, drives the screw movement by rotation, the piston is arranged in the drug storage unit, the screw advances the piston to move; a driving unit, cooperated with the driving wheel; a power unit, connected to the driving unit; a control unit, controlling the driving unit to output forces in two different directions on the driving unit; and sensing unit, operatively connected to the control unit and used to sense or recognize the user's body movements, and different body movements represent different functional instructions, and according to the body movement sensed or recognized by the sensing unit, the control unit controls the infusion unit to execute corresponding functional instructions and manual inputting, the user or the system can flexibly select the infusion mode, the user has no need to manually input functional instructions, improving the user experience.

According to an aspect of the present invention, the functional instructions include infusing drug or stopping infusing drug, priming the infusion needle, puncturing or retracting the infusion needle, adjusting the infusion speed or infusion mode, adjusting the amount of drug infusion, turning on or off the alarm, connecting or disconnecting the remote device, switching the user's physical state, or starting the event.

According to an aspect of the present invention, the sensing unit is provided with one or more of acceleration sensor, inclination sensor, vibration sensor and rotation sensor.

According to an aspect of the present invention, the body movements include one or a combination of jumping, squatting, leg movements, arm movements, taps on the sensing unit, bending over, torso twist, special way of walking.

According to one aspect of the present invention, the body movement sensed or recognized by the sensing unit within a fixed time period t is recognized as a valid body movement, and beyond the fixed time period t, the body movement is recognized as an invalid body movement.

According to one aspect of the present invention, the fixed time period t is 0.5 s-5 s.

According to one aspect of the present invention, the fixed time period t is 1 s.

According to an aspect of the present invention, the sensing unit is integrated in the infusion unit or control unit.

According to an aspect of the present invention, the sensing unit, the control unit and the infusion unit are arranged in one device.

According to an aspect of the present invention, the infusion unit and the control unit are designed separately, and the control mechanism module can be reused.

According to an aspect of the present invention, the infusion unit and the control unit are disposed in one housing, discarded together after a single use.

According to an aspect of the present invention, it further includes a body movement verification unit which is connected to the sensing unit.

According to an aspect of the present invention, the driving member have a variety of different operating modes, thereby making the infusion system have various different infusion increments or infusion rates.

Compared with the prior art, the technical solution of the present invention has the following advantages:

In the bilaterally driven drug infusion system disclosed by the present invention, the sensing unit operatively connected to the control unit and used to sense or recognize the user's body movements, and different body movements represent different functional instructions, and according to the body movement sensed or recognized by the sensing unit, the control unit controls the infusion unit to execute corresponding functional instructions. Compared with manual inputting, body movements are directly used as functional instructions, avoiding the user from searching the inputting position of the functional instructions on the remote device, which is simple and convenient, and improves the user experience as well.

Furthermore, the body movements include one or a combination of jumping, squatting, leg movements, arm movements, taps on the sensing unit, bending over, torso twist, special way of walking. There are many types of body movements which are relatively easy to be performed by users. At the same time, the combination of multiple body movements also improves the flexibility in the manufacturing process in the factory or the operating process for user. And generally, the more types of body movements included by one functional instruction, the safer of the artificial pancreas while executing them.

Furthermore, the sensing unit is provided with one or more of the acceleration sensor, inclination sensor, vibration sensor and rotation sensor. A variety of motion sensors can be selected and combined to improve the accuracy and sensitivity of identifying body movements.

Further, the acceleration sensor is a three-axis acceleration sensor. The three-axis acceleration sensor can detect the change of acceleration in X, Y and Z axes, with the advantage of rapid detection of body movements, improving the sensitivity of movement detection.

Further, the body movements sensed or recognized within a fixed time period t by the sensing unit are recognized as valid movements, beyond the fixed time period t, the body movements by the sensing unit are recognized as invalid movements, which prevents the execution of false instructions from excess body movements of users, and improves the security of the system.

Furthermore, the sensing unit is integrated in the infusion unit or the control unit, or the sensing unit, control unit, sensor and infusion unit are arranged in a single device. The integrated design of multiple units in a single device can improve the integration degree of the infusion system, which facilitates the user's daily physical activities, and further enhances the user experience.

Furthermore, the infusion system further includes a body movement verification unit which is connected to the sensing unit. The movement verification unit is used to confirm whether the user's body movements meet the standard or the requirements preset in this unit, improving the safety of the infusion system infusion system.

Furthermore, the driving unit has a variety of different pivot amplitudes, that is, the driving unit can realize multiple-mode pivot, thereby achieving increment-adjustable infusion. In addition, the driving unit also includes various movement rates, which makes the infusion process more flexible and controllable and significantly improves the efficiency of drug infusion. At the same time, this invention also reduces the minimum drug infusion dosage, accurately controls the process of the drug infusion, effectively avoids large fluctuations of concentration of some substance(s) in patient's body fluid and enables the patients to control and manage their physiological condition more precisely.

DETAILED DESCRIPTION

Figure 1A:
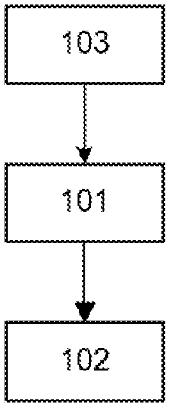
FIG. 1*a* is a schematic view of the unit structure of a bilaterally driven drug infusion system according to an embodiment of the present invention.

As previously mentioned, when a user uses the prior art infusion system, he needs to find different inputting positions on the remote device to manually input functional instruction, and then control the infusion pump to perform corresponding functions. This inputting process is cumbersome, which worsens the user experience.

In order to solve this problem, the present invention provides a bilaterally driven drug infusion system, the sensing unit operatively connected to the control unit and used to sense or recognize the user's body movements, and different body movements represent different functional instructions, and according to the body movement sensed or recognized by the sensing unit, the control unit controls the infusion unit to execute corresponding functional instructions. Compared with manual inputting, body movements are directly used as functional instructions, avoiding the user from searching the inputting position of the functional instructions on the remote device, which is simple and convenient, and improves the user experience as well.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

Figure 1B:
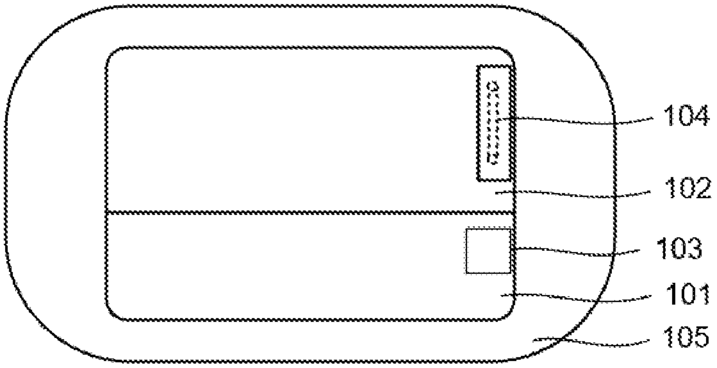
FIG. 1*b*-FIG. 1*e* are schematic top views of a bilaterally driven drug infusion system, respectively, according to four different embodiments of the present invention.
Figure 1C:
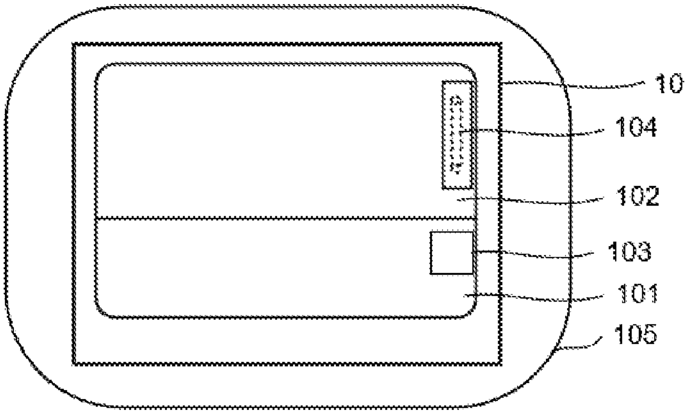
Figure 1D:
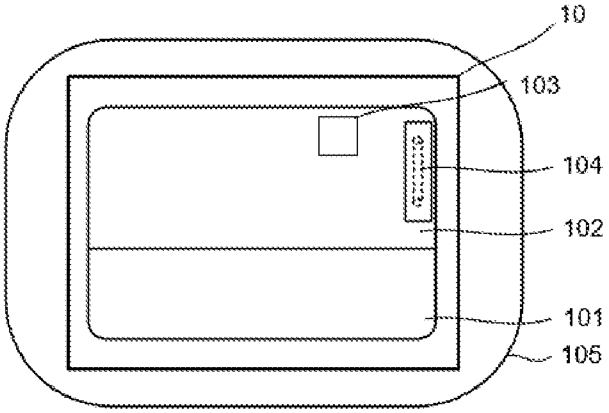

FIG. 1*a* is a schematic view of the unit structure of a unilateral driven drug infusion system according to an embodiment of the present invention; FIG. 1*b*-FIG. 1*d* are schematic top views of a unilateral driven drug infusion system, respectively, according to four different embodiments of the present invention.

The unilateral driven drug infusion system includes an adhesive patch 105, control unit 101, infusion unit 102 and sensing unit 103.

The control unit 101 is used to control the driving power output by the linear actuator or by the reset unit inside the infusion unit 102 to control the drug infusion. The control unit 101 can also establish wireless communication with a remote device, and the like.

The infusion unit 102 includes various units for realizing the function for drug infusion, which will be described in detail below.

The sensing unit 103 is used to sense and recognize body movements from the user, provided with one or more of acceleration sensor, inclination sensor, vibration sensor and rotation sensor.

In the embodiment of the invention, the sensing unit 103 is only provided with a three-axis acceleration sensor, which can detect the change of acceleration in X, Y and Z axis directions, and has the advantage of rapid detection of body movements, more comprehensive recognition of body movements, and improved sensitivity of movement detection.

In another embodiment of the invention, the sensing unit 103 is only provided with rotation sensor, which can accurately detect the user's rotation and other body movements, such as turning in a circle, etc.

In another embodiment of the invention, the sensing unit 103 is only provided with a vibration sensor, and the vibration sensor can accurately detect the user's flapping and other body movements.

In another embodiment of the invention, the sensing unit 103 is provided with a combination of a three-axis acceleration sensor, a rotation sensor and a vibration sensor. The combined motion sensor can realize more and more accurate detection of body movements, enrich the choice of the user and improve the user experience.

The control unit 101 and the sensing unit 103 are operatively connected to facilitate the transmission of instruction signals between the two units. Here, the term "operatively connected" means that the control unit 101 can directly or indirectly obtain body movement information from the sensing unit 103, thereby controlling the infusion unit 102 to perform the corresponding functional instructions, which will be described below in conjunction with different embodiments.

In the embodiment of the present invention, the sensing unit 103 are connected to control unit 101. Herein, the term "connected" means that the control unit 101 and the infusion unit 102 are electrically or wirelessly connected to each other. And the "connected" of any two units or any two structures hereinafter has the same meaning.

Preferably, in the embodiment of the present invention, the sensing unit 103 and the control unit 101 are electrically connected. The electrical connection between the two not only facilitates structural design, but also reduces power consumption compared with the wireless connection. Therefore, the control unit 101 can control the infusion unit 102 to execute corresponding functional instructions, as shown in FIG. 1*a*.

Obviously, in the embodiment of the present invention, the functional instructions include the functions that the infusion unit 102 can perform, such as including but not limited to infusing drug or stopping infusing drug, priming the infusion needle, puncturing or retracting the infusion needle, adjusting the infusion speed or infusion mode, adjusting the amount of drug infusion, starting the event, switching the user's physical state, and connecting or disconnecting the remote device.

In the embodiment of the present invention, the infusion of drugs includes basal dose infusion and bolus dose infusion. Adjusting the infusion speed or the infusion mode means that according to the user's physical state, the user reasonably selects or the artificial pancreas auto-selects the driving type or the driving mode of the driving unit in the infusion unit 102, thereby achieving the goal of optimal blood glucose (BG) controlling. Connecting or disconnecting the remote device means that the user can choose whether to connect the infusion unit 102 to the remote device according to actual needs. Switching the user's physical state means that the user switches from the sitting state to the sleeping state, or from the sleeping state to the wake-up state, etc. Starting the event means indicating the user's meal event, sports event, or bathing event.

The functions performed by the bilaterally driven drug infusion system in the embodiment of the present invention are controlled by the user's body movements. Therefore, in the embodiment of the present invention, different body movements of the user represent different functional instructions. In the embodiment of the present invention, the body movement includes one or a combination of jumping, squatting, leg movements, arm movements, taps on the sensing unit, bending over, torso twist, special way of walking. Compared with manual inputting, body movements are much easier to implement, which improves the user experience.

It should be noted here that tapping the sensing unit 103 not only includes direct contact with the sensing unit 103, but also includes indirect contact or non-contact. For example, the user can tap the clothing around the sensing unit 103. Leg movements include, but are not limited to, raising the leg and shaking the leg. Arm movements include, but are not limited to, vibrating arms and swinging arms. Special walking methods include, but are not limited to, forward and backward walking, circle walking and zigzag.

In the embodiment of the present invention, the functional instructions are represented by single movement or a combination of multiple movements among the above-mentioned body movements, and no limit is set on the frequency of a certain body movement. Preferably, in the embodiment of the present invention, the functional instruction for priming the infusion needle is to tap the sensing unit 103 three times. Tapping three times is chosen instead of one, two, or more than three times, which avoids the interference caused by accidental movements, and is more convenient and more user-friendly than tapping more than three times. In another embodiment of the present invention, the functional instruction for the basal dose infusion is that the user bends down first, and then twists the torso twice. In still another embodiment of the present invention, the functional instruction for connecting or disconnecting the remote device (such as a Personal Diabetes Manager (PDM), mobile phone, ipad, etc.) is zigzagging.

In order to avoid the interference caused by unnecessary or wrong body movements, users need to complete the body movements corresponding to the expected instructions within a fixed time period t. Here, the fixed time period t can be set to any time within 0.5 s-5 s according to the habits of users. Preferably, t=1 s. For example, in the embodiment of the present invention, the user taps the sensing unit 103 three times within 1 s, which is a valid body movement to perform the function instruction of calibrating the infusion unit 102, but because of external factors, the user taps the sensing unit 103 one more time after 1 s, this is an invalid body movement. If there is no fixed time period t to limit, the body movement combination may be recognized as other functional instructions.

It should be noted that the body movements or the combination of body movements corresponding to the above functional instructions are not unique. Users can set the corresponding body movements or the combination of body movements according to their own habits and condition.

In the embodiment of the present invention, the infusion unit 101 and the control unit 102 are designed separately and connected by a waterproof plug or directly engaged and electrically connected into a whole. the infusion unit 101 can be reused, the infusion unit 102 is discarded after a single use. The sensor unit 103 is integrated in the control unit 101 or the infusion unit 102, and attached to a certain position of the user's skin by the adhesive patch 100. Preferably, the sensor unit 103 is integrated in the control unit 100, which can be reused with the control unit 101 to reduce user's use cost, as shown in FIG. 1B. In another embodiment of the present invention, the sensor unit 103 is directly integrated in the control unit 101 or the infusion unit 102, but the control unit 100 and the infusion unit 101 are disposed in one device 10 and connected with a wire, attached to a certain position of the user's skin by the adhesive patch 105, and discarded together after a single use, as shown in FIG. 1*c* and FIG. 1*d*.

Figure 1E:
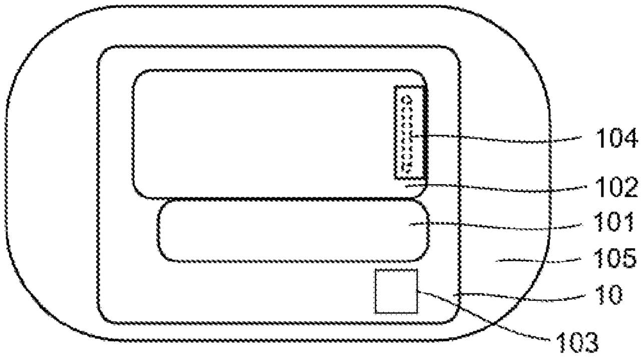

In the other embodiment of the present invention, the sensor unit 103 isn't integrated in the control unit 101 or the infusion unit 102 directly, but the sensing unit, the control unit and the infusion unit are arranged in one device 10, the infusion unit 101 and the control unit 102 can be designed separately or together, that is connected with a wire, and attached to a certain position of the user's skin by the adhesive patch 105, discarded together after a single use, as shown in FIG. 1*e*.

The integrated design of multiple units in a single device can improve the integration degree of the infusion system, which facilitates the user's daily physical activities, and further enhances the user experience.

Figure 2A:
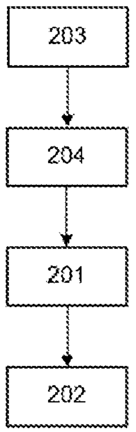
FIG. 2*a*-FIG. 2*b* are schematic views of the unit structure of a bilaterally driven drug infusion system including a movement verification unit according to two different embodiments of the present invention.
Figure 2B:
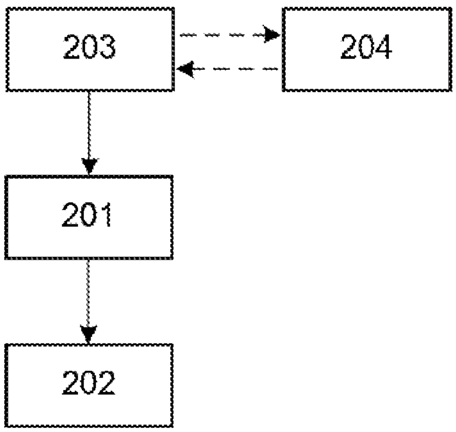

FIG. 2*a*-FIG. 2*b* are schematic views of the unit structure of a unilateral driven drug infusion system including a movement verification unit according to two different embodiments of the present invention.

The movement verification unit 204 is connected with the sensing unit 203 and is used to confirm whether the user's body movements meet the standard or the requirements (such as speed, intensity, or frequency preset), so as to improve the safety of drug infusion system. When the sensing unit 203 detects a user's specific body movement which does not meet the preset requirements or the standard, the drug infusion system will issue a specific form of alarm (such as light, sound, vibration, etc.), allowing the user to perform more standard body movement again. Similarly, when the body movement meets the requirements or the standard, the artificial pancreas can also send out a specific form of warning (such as light, sound, vibration, etc.).

The embodiment of the present invention does not specifically limit the position of the movement verification unit 204 and its connection relationship with other units, as long as the condition for the movement verification unit 204 to be connected to the sensing unit 203 can be met. Preferably, in the embodiment of the present invention, the movement verification unit 204 is provided between the sensing unit 203 and the control unit 201, as shown in FIG. 2*a*. Therefore, after the sensing unit 203 senses or recognizes the user's body movement, the movement verification unit 204 confirms whether the movement meets the requirements or the standard. If met, the control unit 201 receives the body movement information indirectly from the sensing unit 203, thereby controlling the infusion unit 202 to execute the corresponding functional instruction. At this time, sensing unit 203 is operatively connected with the control unit 201.

In another embodiment of the present invention, the movement verification unit 204 may also only be connected to the sensing unit 203, as shown in FIG. 2*b*. When the movement verification unit 204 confirms that the body movement meets the requirements or the standard, the control unit 201 can obtain the corresponding instruction information directly, and then control the infusion unit 202 to execute the corresponding functional instruction.

As mentioned above, here, "connected" refers to that the movement verification unit 204 and the sensing unit 203 are electrically or wirelessly connected to each other.

The bilaterally driven drug infusion system further comprises an infusion needle 104. One end of the infusion needle 104 is connected to the outlet of the reservoir, while the other end pierces the skin to infuse the drug subcutaneously. In the embodiment of the present invention, the infusion needle 104 is disposed at one end of the infusion unit 102. In other embodiments of the present invention, the infusion needle 104 may be disposed at other positions according to its functions or structural features of the device, such as being disposed at the middle portion of the device, which is not specifically limited herein. The infusion needle 104 is a rigid infusion needle or a flexible infusion needle, or designed according to its different positions and functions, the design of infusion needle 104 can also adopt a combination of rigid infusion needle(s) and flexible infusion needle(s), which is not specifically limited herein. Preferably, in the embodiment of the present invention, the infusion needle 104 is a rigid infusion needle.

Figure 3:
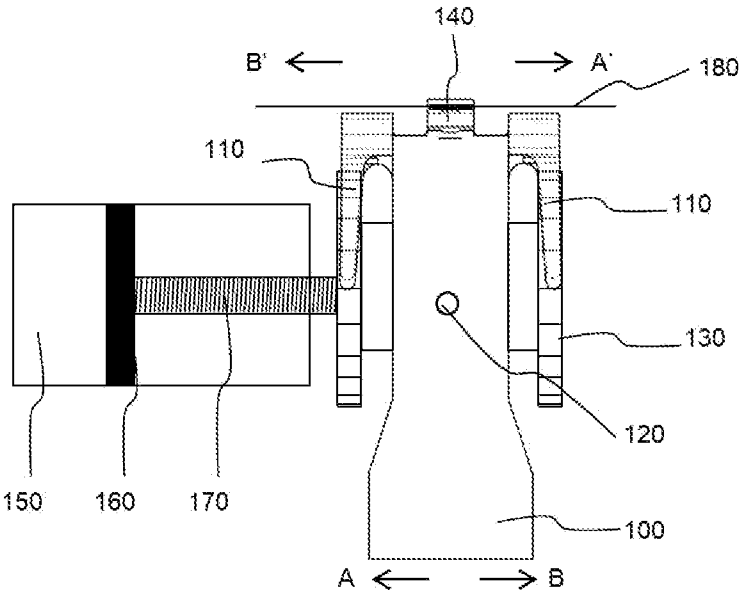
FIG. 3 is a top view of a drug storage unit, a piston, a screw, a driving unit, a power unit, and a driving wheel in a bilaterally driven drug infusion system according to an embodiment of the present invention.

FIG. 3 is a top view of an infusion device according to an embodiment of the present invention. The infusion device includes a driving unit 100, a driving wheel 130, a drug storage unit 150, a piston 160, a screw 170, and a power unit 180.

The screw 170 is coupled to the piston 160 and the driving wheel 130, respectively. In the embodiment of the present invention, the driving wheel 130 is movably mounted on the device base 190, and the driving wheel 130 moves the driving screw 170 through rotation to advance the piston 160 disposed in the drug storage unit 150 to move forward for the purpose of injecting drugs.

The driving unit 100 cooperates with the driving wheel 130. Here, the cooperation means that the movements of both the driving unit 100 and the driving wheel 130 are interrelated to each other.

Figure 8:
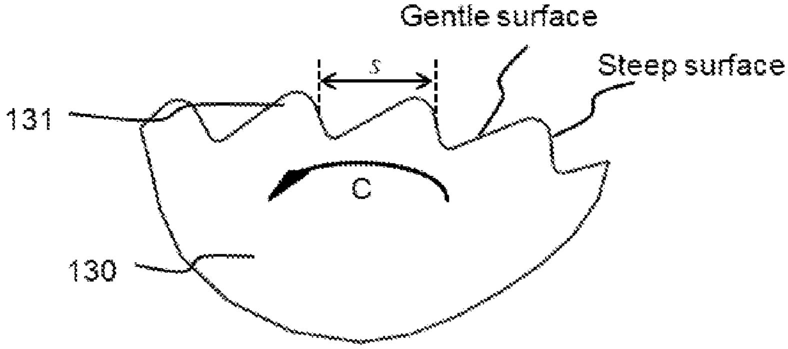
FIG. 8 is a partial schematic structural view of a driving wheel in a bilaterally driven drug infusion system according to an embodiment of the present invention.
Figure 9:
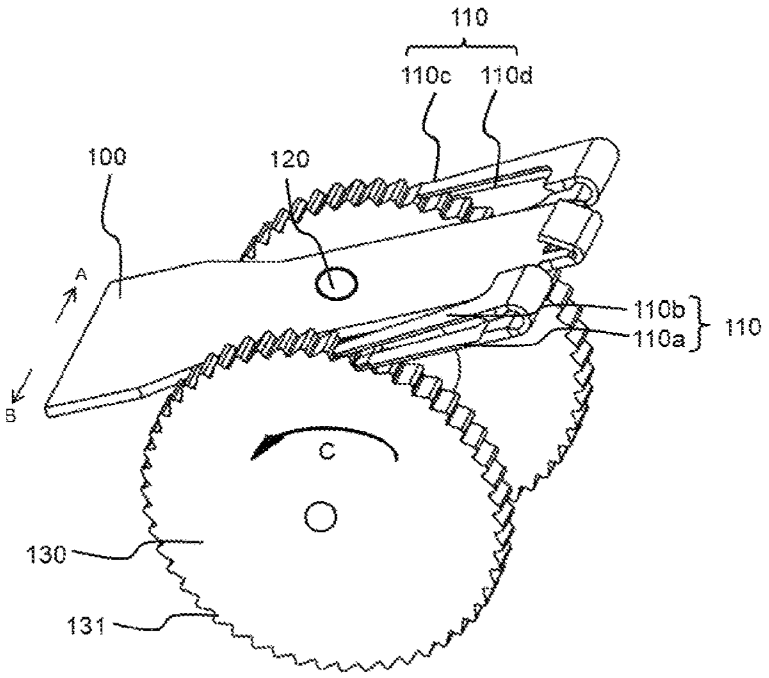
FIG. 9 is a schematic structural view of a driving unit engaging a driving wheel in a bilaterally driven drug infusion system according to an embodiment of the present invention.

In the embodiment of the present invention, the driving wheel 130 is provided with wheel teeth 131 (as shown in FIG. 8 and FIG. 9). The driving unit 100 is movably connected to the base 190 through a pivot shaft 120, and the driving unit 100 can pivot around the rotating shaft 120. The driving unit 100 includes at least two driving arms 110. The pivoting driving unit 100 drives the driving arm 110 to engage the wheel teeth 131 forward to rotate the driving wheel 130.

The power unit 180 outputs two different directional forces on the driving unit 100, making the driving unit 100 have different multiple-mode operation. Here, the operation mode includes the amplitude or rate of the movement. Therefore, the multiple-mode operation of the driving unit 100 includes various movement amplitudes or movement rates, which will be described in detail below.

Specifically, in the embodiment of the present invention, the power unit 180 is fixedly connected at the top position 140 of the driving unit 100, thereby dividing the power unit 180 into two left and right portions, such as the A' direction portion and the B' direction portion in FIG. 3. The driving unit 100 is alternately led to pivot in the A' direction or the B' direction through the pivot shaft 120. Specifically, in the embodiment of the present invention, when the power unit 180 leads the driving unit 100 to A' direction, the driving unit 100 pivots in A direction through the pivot shaft 120. When the power unit 180 leads the driving unit 100 in the B' direction, the driving unit 100 pivots in B direction through the pivot shaft 120. By alternately leading the driving unit 100 in A' direction and B' direction, the driving unit 100 can alternately pivot through the pivot shaft 120 in the A direction and the B direction.

Specifically, in the embodiment of the present invention, the power unit 180 is made of shape memory alloy. The A' direction portion and the B' direction portion of the shape memory alloy are alternately powered on and off, and a leading force is applied to the driving unit 100 by a change in the length of the power unit 180 thereof. The power unit 180 may be composed of one piece of shape memory alloy, or may be composed of left and right segments (such as the A' direction segment and the B' direction segment) of shape memory alloy, and is not specifically limited herein, as long as the force can be applied to lead the driving unit 100 pivot.

Here, it should be noted that the power unit 180 includes but is not limited to a shape memory alloy. In other embodiments of the present invention, the power unit 180 may also be other structures, and the location where the power unit 180 applies force to the driving unit 100 is also not limited to the top position 140, as long as the action of applying a force to the driving unit 100 can be satisfied to cause the driving unit 100 to alternately pivot left and right.

Obviously, by controlling the control unit 101 to control the magnitude of the power output of the power unit 180, the driving unit 100 will have various movement amplitudes. As in the embodiment of the present invention, by controlling the magnitude of the current, the length of the shape memory alloy will change, changing the magnitude of the power and the movement amplitude of the driving unit 100. Therefore, the driving unit 100 has various movement amplitudes. One movement amplitude of the driving unit 100 corresponds to one kind of pivot mode, and therefore, the driving unit 100 has multiple-mode pivot.

Similarly, by controlling the frequency of the power output by the power unit 180, the driving unit 100 will have various movement rates. As in the embodiment of the present invention, by changing the energization frequency, the frequency of the power output also changes, thus changing the movement rate of the driving unit 100 accordingly.

Figure 4A:
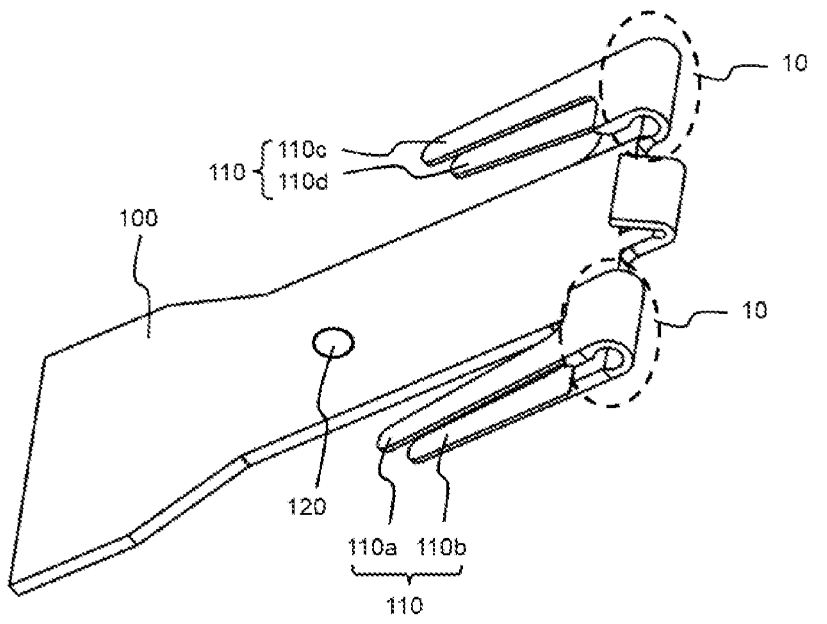
FIG. 4*a*-FIG. 4*c* are respectively a schematic structural view of a three-dimensional structure, a side view and a top view of a driving unit in a bilaterally driven drug infusion system according to an embodiment of the present invention.

Referring to the perspective view of the driving unit 100 shown in FIG. 4*a*, the driving unit 100 further includes more than two driving arms 110. The driving wheel 130 includes a plurality of sub-wheels. Referring to the structure shown in FIG. 3 and FIG. 4*a*, when a plurality of driving arms 110 are installed on one side of the driving unit 100, the driving unit 100 can drive the driving arms 110 to engage the wheel teeth 131 through adjustable pivoting to rotate the driving wheel 130 by an optional number of teeth. Thus, in an embodiment of the invention, the driving unit 100 and the driving wheel 130 are designed to work compatibly, which means that the position of the driving wheel 130 and the number of the sub-wheels need to be compatible with the working principle of the driving unit 100 and the number, position and structure of the driving arms 110.

As shown in FIG. 3 and FIG. 4*a*, in the embodiment of the present invention, a plurality of driving arms 110 are installed on each side of the driving unit 100. Therefore, a plurality of sub-wheels are also installed on both sides of the driving unit 100 to cooperate with the driving arms 110. Specifically, in the embodiment of the present invention, the driving unit 100 includes four driving arms 110, which are 110*a*, 110*b*, 110*c*, and 110*d*, respectively. 110*a*, 110*b* are installed on one side of the driving unit 100, while 110*c*, 110*d* are installed on the other side of the driving unit 100. The driving wheel 130 includes two sub-wheels, one of which cooperates with 110*a*, 110*b* and the other of which cooperates with 110*c*, 110*d*.

It should be noted that the driving wheel 130 may further include more than two sub-wheels. For example, according to the design of the position and structure of the plurality of driving arms 110, two adjacent sub-wheels may be set on one side of the driving unit 100 to cooperate with different positions, numbers of driving arms 110 on this side of the driving unit 100.

Figure 4B:
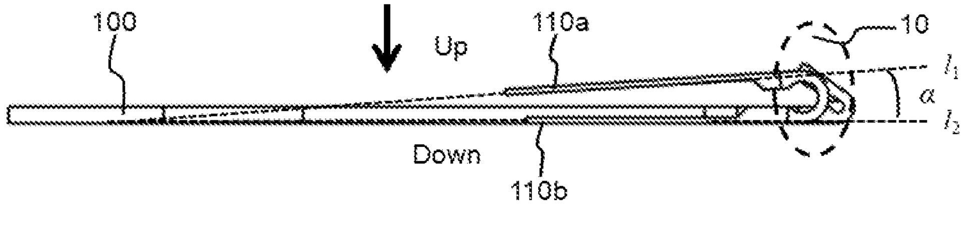
Figure 4C:
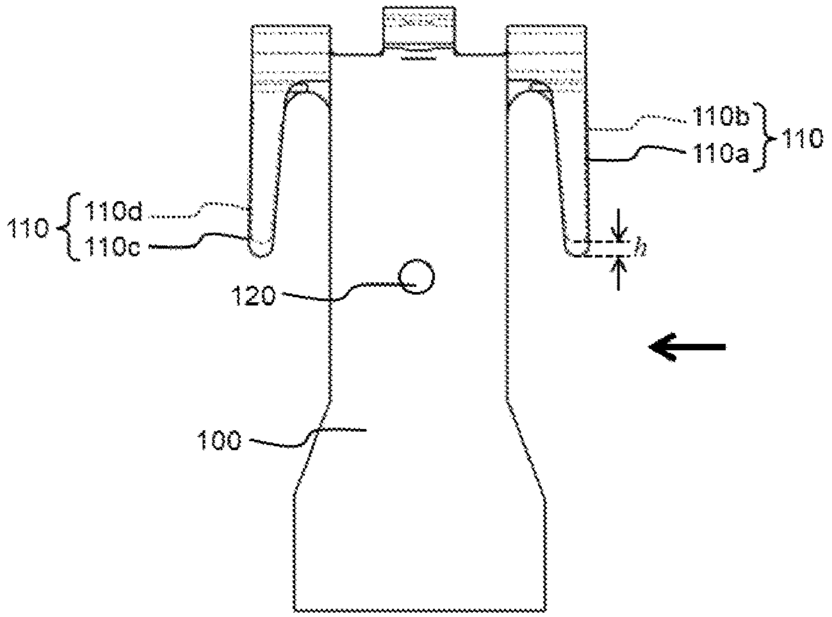

FIG. 4*a*, FIG. 4*b*, and FIG. 4*c* are respectively a schematic view of a three-dimensional, a side view, and a top view of the driving unit 100, and the top view direction of FIG. 4*c* is the direction indicated by the arrow in FIG. 4*b*, while the side view direction of FIG. 4*b* is the direction shown by the arrow in FIG. 4*c*.

In the embodiment of the present invention, the two driving arms 110 on one side of the driving unit 100 are installed up and down. Here, the up and down settings refer to the up and down positional relationship representations shown in FIG. 4*b*. Specifically, the two driving arms 110 (such as 110*a* and 110*b*) on the side of the driving unit 100 can be seen in the side view FIG. 4*b*, and in the top view FIG. 4*c*, 110*b* and 110*d* are blocked by 110*a* and 110*c*, respectively, wherein 110*b* and 110*d* are indicated by dotted lines in FIG. 4*c*.

In the embodiment of the present invention, since the driving wheel 130 is circular, the surfaces on which the adjacent teeth are applied with the engaging force are not parallel. Therefore, in order to keep the angle between the driving arms 110 and the teeth engaging surface 90 degree during engaging, thereby improving the engaging efficiency of the driving arms 110, when the driving arms 110 on one side of the driving unit 100 engage the wheel teeth 131, the lines representing the engaging directions of the two driving arms 110 intersect each other. Specifically, as shown in FIG.

4*b*, when the wheel teeth 131 are engaged by 110*a* and/or 110*b*, the straight line where 110*a* is located is $l_1$, the straight line where 110*b* is located is $l_2$, wherein the angle between $l_1$ and $l_2$ is $\alpha$, $3.1° \leq \alpha \leq 4.1°$. Specifically, in the embodiment of the present invention, $\alpha=3.5°$. In another embodiment of the invention, $\alpha=3.3°$. In still another embodiment of the invention, $\alpha=3.9°$.

It should be noted that, in other embodiments of the present invention, according to different structural designs, when the driving arms 110 on one side of the driving unit 100 engage the wheel teeth 131, the lines representing the engaging directions of these two driving arms 110 can also be parallel ($\alpha=0°$) or skew with a structure also able to drive the driving wheel 130 to rotate to achieve the purpose of drug infusion. In this case, the angle $\alpha$ between $l_1$ and $l_2$ may be set according to the actual structure, such as according to the diameter, number of the driving wheel 130, the number of the wheel teeth 131, the pitch of the screw 170, the positional relationship and the number of the driving arms 110. For example, $\alpha$ may be between 0°~3.1° or $4.1°<\alpha\leq 7°$, and is not specifically limited herein.

Figure 5A:
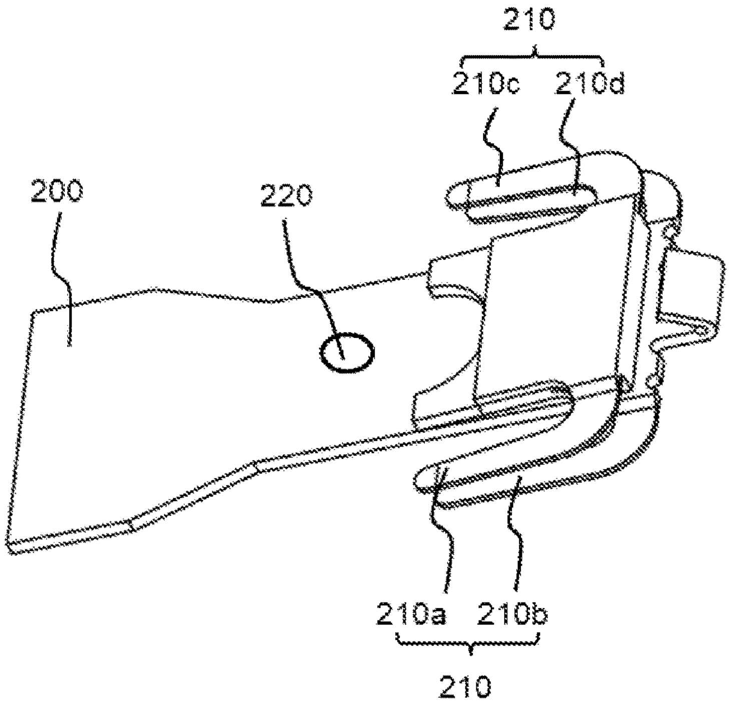
FIG. 5*a*-FIG. 5*b* are schematic structural view of a driving unit of a bilaterally driven drug infusion system according to another embodiment of the present invention.
Figure 5B:
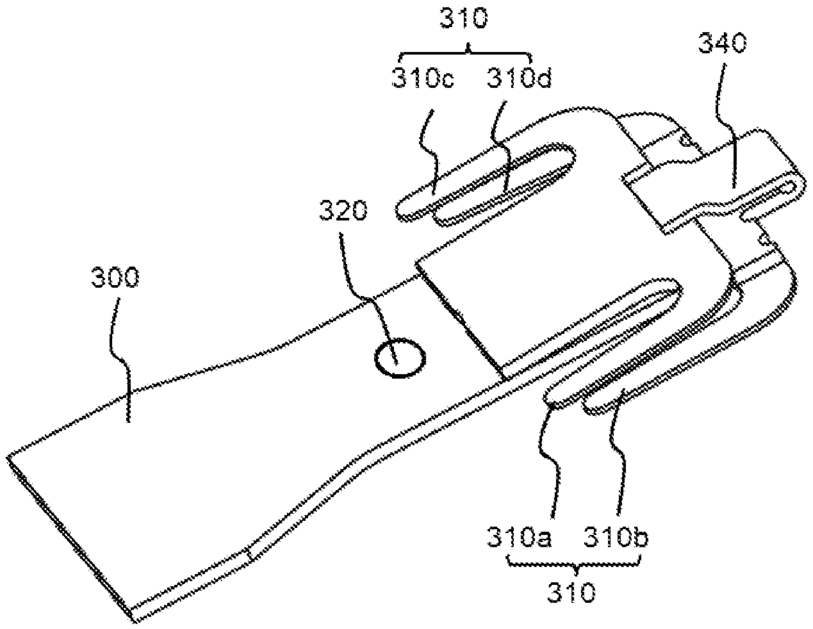

As shown in the dotted portion 10 of FIG. 4*a* and FIG. 4*b*, in the embodiment of the present invention, the two driving arms 110 on one side of the driving unit 100 are formed by folding at the dotted circle 10. In other embodiments of the present invention, the two driving arms 110 on one side of the driving unit 100 may also be formed by other means. As shown in the perspective view of the driving unit shown in FIG. 5*a* and FIG. 5*b*, the up position 210*a*, 210*c* and the down position 210*b*, 210*d* are respectively set in different structural subunits. As in FIG. 5*a*, the two structural subunits are secured together by welding or other means of attachment to form one single structure. And as shown in FIG. 5*b*, the two structural subunits are connected at the top position 340 of the driving unit 300, and then the top position 340 of the driving unit 300 is folded over to form the structure of the driving arms 310 in the embodiment of the present invention.

It should be noted that, in other embodiments of the present invention, the driving arms may be formed by other means, as long as the arms are able to drive the driving wheel to rotate, and is not specifically limited herein.

Figure 6:
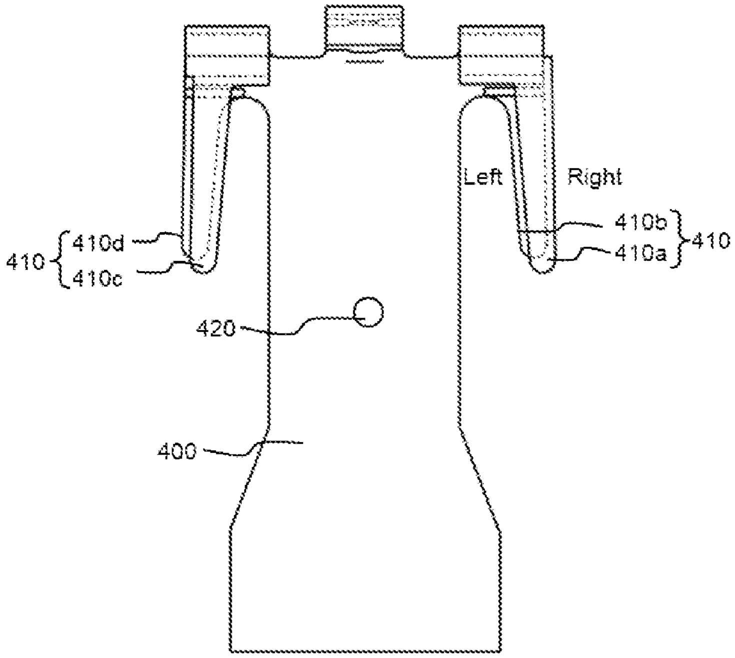
FIG. 6 is a schematic structural view of a driving unit in a bilaterally driven drug infusion system according to another embodiment of the present invention.

Please refer to FIG. 6, which is a top view of a driving unit 400 according to another embodiment of the present invention.

The angles of view of FIG. 6 and FIG. 4*c* are the same. According to FIG. 4*a*, FIG. 4*b*, FIG. 4*c* and FIG. 6, it is apparent that the two driving arms on one side of the driving unit 400 are slightly offset from left and right, such as 410*a*, 410*b* and 410*c*, 410*d*. Specifically, in one embodiment of the invention, 410*a* and 410*c* are offset to the right and 410*b* and 410*d* are offset to the left.

It should be noted that, in other embodiments of the present invention, the left and right offset degree of the two driving arms on the same side and the direction in which the two are offset relative to each other need to be determined according to the actual structural design, and are not limited specifically described herein. Furthermore, in an embodiment of the invention, the two driving arms on one side of the driving unit can also be installed left and right. Here, the left and right installing mean that from the perspective of FIG. 6 (top view), two complete driving arms on one side of the driving unit can be seen, while from the perspective of FIG. 4*b* (side view), the driving arms close to the main body of the driving unit is completely or partially blocked by the driving arms away from driving unit's main body. In this case, the lines presenting the engaging directions of driving arms on the same side of driving unit is coplanar or skew. At the same time, there is no particular limitation on the length or the length relationship among different driving arms.

Figure 7:
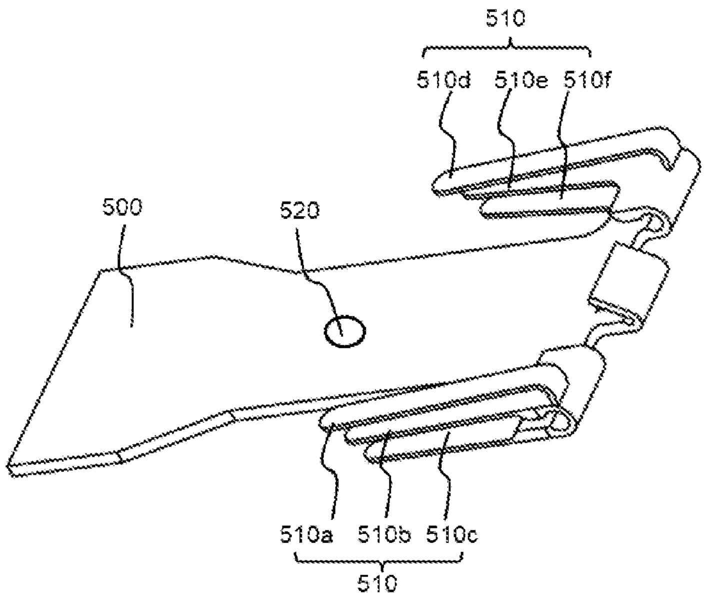
FIG. 7 is a schematic structural view of a driving unit in a bilaterally driven drug infusion system according to another embodiment of the present invention.

Please refer to FIG. 7, which is a schematic perspective view of a driving unit 500 according to still another embodiment of the present invention.

Specifically, the driving unit 500 includes six driving arms 510, each three of which are installed on one side of the driving unit 500. Specifically, 510*a*, 510*b*, and 510*c* are installed on one side, and 510*d*, 510*e*, and 510*f* are installed on the other side. As described above, the lengths, the length relationships and the positional settings of the driving arms 510 on the same side are designed according to the specific structure and working principle, and are not specifically limited herein. Specifically, in the embodiment of the present invention, the positional relationship of the three driving arms 510 on the same side of the driving unit 500 is similar to that in FIG. 4*a*, FIG. 4*b* and FIG. 4*c*, that is, the three driving arms 510 on the same side of the driving unit 500 are installed up and down.

It should be noted that, in other embodiments of the present invention, the total number of driving arms may also be an odd number, such as three, five or more, that is, the numbers of driving arms on both sides of the driving unit are not equal. Moreover, the structural relationship between the different driving arms can be similar to that described above, and no specific restrictions are imposed here.

Referring to FIG. 8 and FIG. 4*c* together, FIG. 8 is a partial structural diagram of the driving wheel 130, and wheel teeth 131.

In the perspective of FIG. 4*c*, the horizontal distance between the driving ends of the two driving arms on one side of the driving unit 100 is h, and the pitch of the wheel teeth 131 is s, then $0.5\ s \leq h \leq 1.5\ s$. Specifically, in the embodiment of the present invention, $h=0.8\ s$. In another embodiment of the invention, $h=1.2\ s$. In still another embodiment of the invention, $h=s$. Here, the driving end of the driving arms 110 refers to the end of the driving arms 110 that directly contacts the wheel teeth 131 when engaged. The horizontal distance refers to the distance between two projection points of the driving ends of the two driving arms 110 on the same side of the driving unit 100 on a plane when viewed in an angle as shown in FIG. 4*c*.

It should be noted that in other embodiments of the present invention, $0.1\ s \leq h < 0.5\ s$ or $1.5\ s < h \leq 2.5\ s$ may be used, and the effects of the present invention may be also achieved, and also are not specifically limited herein.

As shown in FIG. 8, in the embodiment of the present invention, the driving wheel 130 is a ratchet, and the wheel teeth 131 are ratchet teeth. Each ratchet tooth surface includes a gentle surface and a steep surface, therefore it's easy to be engaged, as shown in FIG. 8. Moreover, in the embodiment of the present invention, the driving arms 110 of the driving unit 100 include a portion that drives the driving wheel 130 to rotate and a portion that does not drive the driving wheel 130 to rotate during the entire pivot of the driving unit 100 in one direction. The portion that drives the driving wheel 130 to rotate applies the engaging force on the steep surface of the ratchet teeth, in order to drive the driving wheel 130 to rotate in the C direction.

Please refer to FIG. 9, which is a schematic perspective view of the driving unit 100 and the driving wheel 130.

With reference to FIG. 9, FIG. 3, FIG. 4*b* and FIG. 4*c*, in the embodiment of the present invention, under the action of the power unit 180, the driving unit 100 pivots around the pivot shaft 120, thereby driving the plurality of driving arms

110 on both sides of the driving unit 100 to engage the wheel teeth 131 for rotation of the driving wheel 130.

Figure 10:
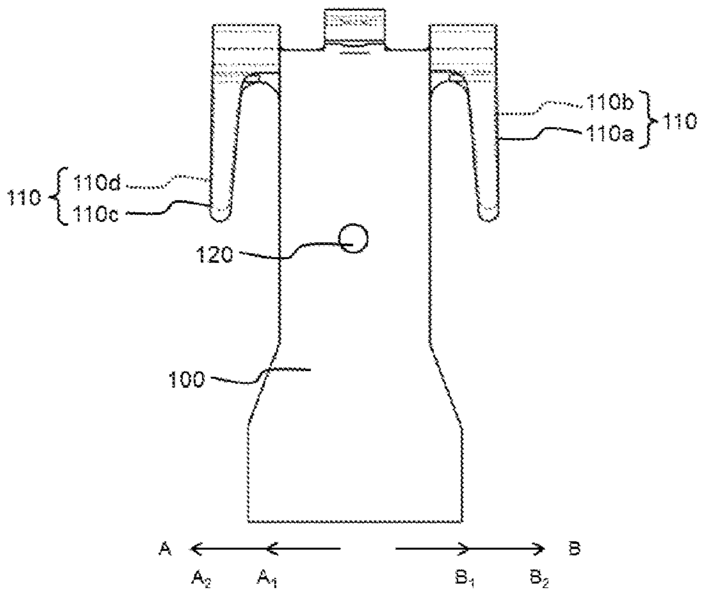
FIG. 10 is a schematic structural view showing a pivoting position of different movement modes of a driving unit in a bilaterally driven drug infusion system according to an embodiment of the present invention.

Referring to FIG. 9 and FIG. 10 together, FIG. 10 is a schematic structural diagram of the adjustable pivoting movements of the driving unit 100

As described above, the driving unit 100 has a certain distance h between the driving ends of the driving arms 110 on the same side, and there is a certain angle α between the lines representing the driving directions when the arms are engaged. And therefore, the driving unit 100 pivots in one direction in a single time throughout the process, as shown in FIG. 9 in a single pivot in the direction A, 110*a* and/or 110*b* engage the wheel teeth 131 to drive the driving wheel 130, while 110*c* and 110*d* can slide on the wheel teeth 131 (as on the gentle surface of the ratchet teeth, but not exert a force for driving the driving wheel 130 to rotate). And obviously, 110*c* slides to the next driving position first. Here, the driving position refers to the position where the driving arm can engage the wheel teeth to advance, so as to the following driving position. At this time, the driving end of 110*c* acts on the steep surface of the ratchet teeth. At this time, the driving unit 100 stops pivoting and the driving arms 110*a* and/or 110*b* stop engaging the wheel teeth 131, and the driving wheel 130 stops rotating. Thus the driving unit 100 completes one step of pivot. Referring to FIG. 10, the driving unit 100 pivots in the A direction to reach $A_1$ position, which corresponds to one kind of pivot amplitude, making the infusion device have an infusion increment. The next moment the driving unit 100 continues to pivot in the A direction, 110*d* will slide to the next driving position. Similarly, the driving end of 110*d* also acts on the steep surface of the ratchet teeth. Thus the driving unit 100 completes a second step of pivot. Referring to FIG. 10, the driving unit 100 still pivots in the A direction to reach $A_2$ position, which corresponds to another kind of pivot amplitude, making the infusion device have another infusion increment. At this time, 110*c* and 110*d* respectively complete the sliding between adjacent wheel teeth 131, and the driving unit 100 completes the whole process of single pivot in the A direction, reaching $A_1$ and $A_2$ positions respectively, thereby driving the driving wheel 130 to rotate by two steps, realizing two-step infusion of the drug device and making the infusion device have two different infusion increments.

It should be noted that, in the above pivoting process, 110*d* may first slide to the next wheel teeth 131, and then 110*c* slide to the next wheel teeth 131, which is not specifically limited herein. Similarly, when the driving unit 100 pivots in the B direction, it can reach $B_1$ and $B_2$ positions respectively, which also corresponds another two infusion increments.

Obviously, in the whole process of the above-mentioned single pivot in the A direction, the driving unit 100 undergoes an alternate action of pivot and stop, and the driving arms 110 alternately engage and stop engaging wheel teeth 131 to drive the driving wheel 130 to rotate and stop rotating, realizing two-step rotation of the driving wheel, and finally achieves two-level increment-adjustable drug infusion.

Specifically, when the driving unit has two driving arms on one side, the driving unit undergoes two-step movement of the pivot-stop-pivot-stop during the single pivot in the A direction, in order to drive driving wheel for two-step rotation. When the driving unit has three driving arms on one side, the driving unit performs the pivot-stop-pivot-stop-pivot-stop three-step motion in the whole process of single pivot in the A direction, realizing three-step rotation of the driving wheel to achieve three-level increment-adjustable drug infusion. By analogy, when there are more driving arms on one side of the driving unit, the driving unit realizes multiple-step driving of the driving wheel by the multiple-step actions of the pivot-stop-pivot-stop-pivot- . . . -pivot-stop, completing multi-level increment-adjustable drug infusion.

With continued reference to FIG. 9, in combination with the above, in the embodiment of the present invention, when the driving unit 100 drives the driving wheel 130 to rotate, at least one of the driving arms 110 on the driving force side applies an engaging force to the wheel teeth 131. While one or both of the driving arms 110 on the other side are in contact with the wheel teeth 131 without applying any force to the wheel teeth 131 to drive the driving wheel 130 to rotate. Therefore, there is a case in the embodiment of the present invention that only one of the driving arms 110 of the driving unit 100 engages the wheel teeth 131 to rotate the driving wheel 130, and the other driving arms 110 are in contact with the driving wheel 130 without applying any force to the wheel teeth 131 to rotate the driving wheel 130.

It should be noted that, in the embodiment of the present invention having three or more driving arms on one side of the driving unit, when the driving unit is in operation, the above-mentioned similar situation may also occur. When there are an odd number of driving arms, the numbers of driving arms on both sides of the driving unit are not equal, and the same process as above is also performed in the whole process of the driving unit rotating in a certain direction.

Referring to FIG. 10 again, in another embodiment of the present invention, when the driving unit 100 has two driving arms 110 on one side, the driving unit 100 pivots one step in the A direction, that is, reaching the $A_1$ position, and then pivots one or two steps in the B direction, that is, reaching the $B_1$ or $B_2$ position until the pivot in the B direction stops, the driving unit 100 pivoting by different amplitudes. This process completes the alternate pivot of the driving unit 100 in two directions, so that the driving wheel 130 can be rotated in multiple steps. Therefore, in the embodiment of the present invention, the driving unit 100 can alternately switch modes among $A_1$-$B_1$ or $A_1$-$B_1$-$B_2$ or $B_1$-$A_1$-$A_2$, so as to achieve the purpose of switching among different increments of infusion.

With continued reference to FIG. 10, in another embodiment of the present invention, the driving unit 100 can also be pivoted directly to the $A_2$ position without passing through the $A_1$ position, then directly pivoted to the $B_2$ position without passing through the $B_1$ position, that is, the driving unit 100 alternately pivots between the $A_2$-$B_2$ positions. As described above, the driving unit 100 can also alternately pivot between the $A_1$-$B_1$ positions. Obviously, in a unit time, the dosage of infused drug when the driving unit 100 alternately pivots between the $A_2$-$B_2$ positions is greater than the dosage of infused drug when it alternately pivots between the $A_1$-$B_1$ positions.

In other embodiments of the present invention, as shown in FIG. 10, after the driving unit 100 pivots in the direction A and the driving arm 110*c* or 110*d* slides to the driving position, the driving unit 100 may continue to pivot in the direction A until both the driving arm 110*c* and 110*d* are away from the driving position, the driving unit 100 stopping pivoting and starting to pivot in the B direction at the next moment. This operation mode enables the driving unit 100 to have more kinds of movement amplitudes, that is, multiple-mode pivot. Obviously, when the driving unit 100 pivots in the direction B for a certain period of time, all the driving arms 110 slide on the surface of the wheel teeth 131, that is, no engaging is performed. For ease of description, the above process will be described in detail below in conjunction with an embodiment in which the driving unit 100 includes only two driving arms.

Figure 11A:
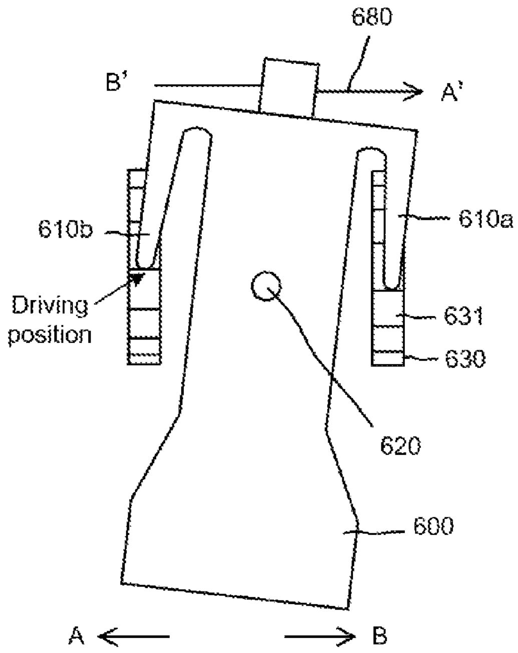
FIG. 11*a*-FIG. 11*c* are schematic structural views of a driving unit including two driving arms in a bilaterally driven multi-infusion mode drug infusion device according to an embodiment of the present invention.
Figure 11B:
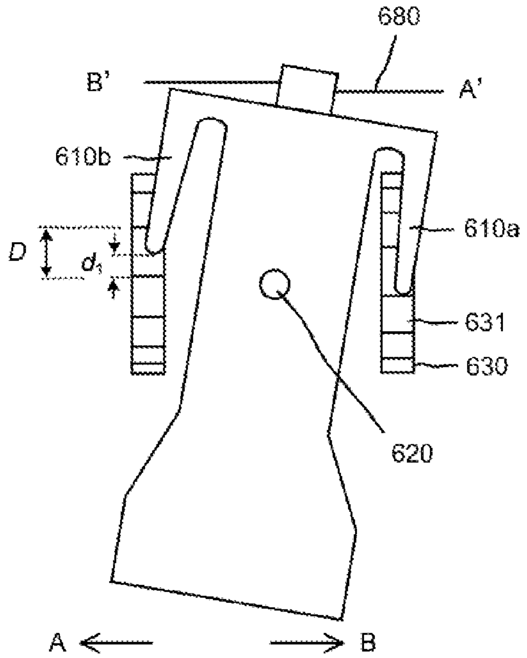
Figure 11C:
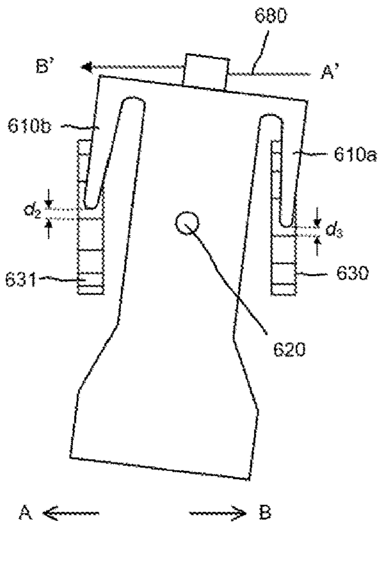

FIG. 11*a*-FIG. 11*c* are schematic structural views of the driving unit 600 including two driving arms 610*a* and 610*b*.

Similar to the driving principle described above, in one embodiment of the present invention, when the control unit 101 controls the power unit 680 apply force to the driving unit 600 in the A' direction, the driving arm 610*a* engages the wheel teeth 631 forward, making the driving unit 600 pivot around the pivot shaft 620 and the driving arm 610*b* sliding on the surface of the wheel teeth 631 until the driving arm 610*b* reaches the driving position, in which the driving unit 600 pivots by a certain amplitude, as shown in FIG. 11*a*. The control unit 101 controls the power unit 680 start to apply force in the B' direction, making the driving arm 610*b* engage the wheel teeth 631 forward. By analogy, the driving unit 600 alternately pivots in two directions.

In the embodiment of the present invention, after the driving arm 610*b* reaches the driving position, the driving unit 600 continues to pivot in the direction A, thus the driving arm 610*b* continuing to slide on the surface of the wheel teeth 631. After the distance between the driving end of the driving arm 610*b* and the steep surface of the wheel teeth 631 is $d_1$, the power unit 680 stops outputting force, which is shown in FIG. 11*b*. At this time, the driving unit 600 pivots by a larger amplitude. If the pitch of the wheel tooth is D, then $d_1=D/n$, $n>1$. Obviously, after the power unit 600 outputs force in the direction of B', both the driving arms 610*b* and 610*a* slide on the surface of the wheel teeth 631 within a period of time after the driving unit 600 starts to pivot, as shown in FIG. 11*c*. The distances between the driving arms 610*b*, 610*a* and the steep surfaces of their corresponding wheel teeth 631 are $d_2$ and $d_3$, respectively. Obviously, $d_2<D$ and $d_3<D$. As described above, when more driving arms are provided on the driving unit 600, a similar situation will occur for each driving arm.

The total distance of the driving arm 610*b* sliding in the above process can be arbitrarily selected, for example, the total sliding distance is 0.4 D, 0.7 D, D (as shown in FIG. 9*a*), 1.5 D, 1.75 D, 2 D, 2.3 D, 2.5 D, etc. The driving unit 600 has various pivot amplitudes, that is, various rotation gears, making the infusion device have multiple infusion increments.

Figure 12A:
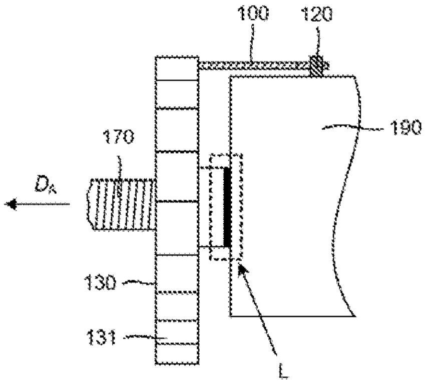
FIG. 12*a*-FIG. 12*b* are schematic structural views of a driving wheel and a base or a limiting member in a bilaterally driven multi-infusion mode drug infusion device according to an embodiment of the present invention.
Figure 12B:
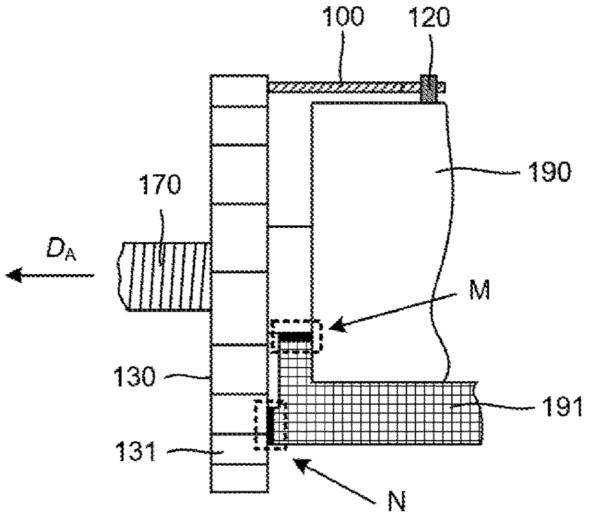

FIG. 12*a* and FIG. 12*b* are schematic diagrams of the driving wheel 130 and the base 190, or the position limited member 191 according to an embodiment of the present invention. FIG. 12*a* and FIG. 12*b* are front views of partial structures in FIG. 3.

When the driving arm 110 slides on the surface of the wheel teeth 131, the driving arm 110, contact with the wheel teeth 131, applies a certain pressure to the driving wheel 130 to ensure the non-rotating of the driving wheel 130. However, it is obvious that due to the structural features of the wheel teeth 131 and the circumference of the driving wheel 130, the pressure applied by the driving arm 110 is not equal at different positions. Therefore, when the driving arm 110 slides (including reset movement or sliding forward) on the surface of the wheel teeth 131, the driving wheel 130 may rotate forward or reverse, which affects the accuracy of the drug infusion volume and brings safety risk.

As shown in FIG. 12*a*, the driving wheel 130 is movably assembled on the base 190 remaining in frictional engagement. Here, the friction fit between these two means a certain friction force preset between two mutually moving structures, so as to the meaning of the following friction fit.

In the embodiment of the present invention, the frictional force of the relative movement between the driving wheel 130 and the base 190 is applied or increased at the position L, indicated by the dotted frame, to ensure that when the driving arm 110 slides on the surface of the wheel teeth 131, the driving wheel 130 stops rotating.

As shown in FIG. 12*b*, in another embodiment of the present invention, the infusion device further includes a position limited member 191 that is movably assembled on the base 190 to limit the position of the driving wheel 130. The position limited member 191 is in friction fit with the driving wheel 130 at position M or position N, indicated by the dotted frame. Similarly, in the embodiment of the present invention, the position limited member 191 increases the frictional force that the driving wheel 130 receives when rotating, also ensuring that the driving wheel 130 stops rotating when the driving arm 110 slides on the surface of the wheel teeth 131. At the same time, the position limited member 191 can make full use of the internal space of the infusion device, and frictionally cooperate with the driving wheel 130 at multiple positions.

Other embodiments of the present invention do not limit the position of the above friction fit, as long as the condition for applying or increasing the friction force received by the second driving unit during movement is satisfied. For example, the friction force can also be applied on both sides of the driving wheel 130 at the same time. The embodiment of the present invention neither limits the material of the position limited member 191. For example, the position limited member 191 is an elastic member, a plastic member or a metal member.

Other embodiments of the present invention may increase the pressure of the driving arm 110 on the wheel teeth 131 instead of providing the above-mentioned friction fit, which can increase the maximum static friction of the driving wheel 130 and also ensure the non-rotating of the driving wheel 130 when the driving arm 110 slides on the surface of the wheel teeth 131.

If the minimum dosage of infused drug driven by the driving unit is the minimum increment of the infusion device, the bilaterally driven drug infusion system using the embodiment of the present invention can reduce the minimum increment of drug dosage and achieve more precise control of the drug infusion. When the patient needs to infuse more drugs, the large $A_2$-$B_2$ mode can be selected to speed up the infusion rate. When a small amount of drug needs to be infused, the patient can select the small $A_1$-$B_1$ mode to reduce the drug infusion rate and achieve precise control of the drug infusion.

Compared with the device with increment-adjustable infusion, in the bilaterally driven drug infusion system, the driving unit performs multiple-mode operation, making the infusion device have multiple infusion increments or infusion rates. With the bilaterally driven drug infusion system of the embodiment of the invention, the patient can freely and flexibly switch between different increments of infusion according to the actual drug dosage and the demand of the infusion rate, thereby improving the infusion efficiency. At the same time, intermediate $A_1$-$B_1$-$B_2$ mode or $B_1$-$A_1$-$A_2$ mode and the small $A_1$-$B_1$ mode are set along with the large $A_2$-$B_2$ mode. And the bilaterally driven drug infusion system can reduce the minimum dosage of infused drug in order to achieve the goal of precise control of the infusion.

As with the bilaterally driven drug infusion system of the embodiment of the present invention, when the infusion is started, the amount of drug required is relatively large, and the patient can select the large $A_2$-$B_2$ mode shown in FIG. 10 for infusion. After a period of infusion, the intermediate $A_1$-$B_1$-$B_2$ mode or $B_1$-$A_1$-$A_2$ mode can be used to reduce the rate of drug infusion. When the drug infusion is about to be completed, the patient can switch to the small $A_1$-$B_1$ mode to further reduce the infusion rate and achieve precise control of the drug infusion. Of course, the patient can also choose one or several of the modes for infusion, and there are no specific restrictions.

In other embodiments of the present invention, when more than two driving arms are installed on one side of the driving unit, the infusion device can have more and more elaborate infusion modes, and the patient can further flexibly control the infusion to make the infusion process more precisely.

In summary, the present invention discloses a bilaterally driven drug infusion system, the sensing unit operatively connected to the control unit and used to sense or recognize the user's body movements, and different body movements represent different functional instructions, and according to the body movement sensed or recognized by the sensing unit, the control unit controls the infusion unit to execute corresponding functional instructions. Compared with manual inputting, body movements are directly used as functional instructions, avoiding the user from searching the inputting position of the functional instructions on the remote device and manual inputting, which is simple and convenient, and improves the user experience as well.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A bilaterally driven drug infusion system, comprising:
- an infusion unit comprising:
  - a drug storage unit;
  - a piston and a driving wheel which are connected with a screw, wherein the driving wheel, provided with wheel teeth, drives the screw to rotate, the piston is arranged in the drug storage unit, the screw advances the piston to move;
  - a driving unit, cooperated with the driving wheel; and
  - a power unit, connected to the driving unit;
- a control unit, controlling the driving unit to output forces in two different directions on the driving unit; and
- a sensing unit, operatively connected to the control unit and used to sense or recognize body movements, wherein the body movements which are different represent different functional instructions, and according to the body movement sensed or recognized by the sensing unit, the control unit controls the infusion unit to execute a corresponding functional instruction of the functional instructions,
  - wherein the sensing unit is integrated in the infusion unit, and the sensing unit and the infusion unit are discarded together after a single use, or
  - the sensing unit is integrated in the control unit, and the sensing unit and the control unit are reusable,
  - wherein the sensing unit is provided with one or more of an acceleration sensor, an inclination sensor, a vibration sensor and a rotation sensor, and the sensing unit directly measures acceleration, inclination, vibration and/or rotation of a user.

2. The bilaterally driven drug infusion system of claim 1, wherein,
the functional instructions include infusing drug or stopping infusing drug, priming an infusion needle, puncturing or retracting the infusion needle, adjusting an infusion speed or an infusion mode, adjusting an amount of drug infusion, turning on or off an alarm, connecting or disconnecting a remote device, switching a physical state, or starting an event.

3. The bilaterally driven drug infusion system of claim 1, wherein,
the body movements include one or a combination of jumping, squatting, leg movements, arm movements, taps on the sensing unit, bending over, torso twist, special way of walking.

4. The bilaterally driven drug infusion system of claim 1, wherein,
the body movement sensed or recognized by the sensing unit within a fixed time period t is recognized as a valid body movement, and beyond the fixed time period t, the body movement is recognized as an invalid body movement, the fixed time period t is 0.5 s-5 s.

5. The bilaterally driven drug infusion system of claim 4, wherein,
the fixed time period t is 1 s.

6. The bilaterally driven drug infusion system of claim 1, wherein,
the sensing unit, the control unit and the infusion unit are arranged in one device.

7. The bilaterally driven drug infusion system of claim 6, wherein,
the infusion unit and the control unit are detachable from each other separately.

8. The bilaterally driven drug infusion system of claim 6, wherein,
the infusion unit and the control unit are disposed in one housing, discarded together after a single use.

9. The bilaterally driven drug infusion system of claim 1, wherein,
the infusion unit and the control unit are detachable from each other.

10. The bilaterally driven drug infusion system of claim 1, wherein,
the infusion unit and the control unit are disposed in one housing, discarded together after a single use.

11. The bilaterally driven drug infusion system of claim 1, further comprising a body movement verification unit which is connected to the sensing unit.

12. The bilaterally driven drug infusion system of claim 1, wherein,
the driving unit have a variety of different operating modes, thereby making the bilaterally driven drug infusion system have various different infusion increments or infusion rates.

* * * * *